(12) United States Patent
Gedon et al.

(10) Patent No.: US 6,242,627 B1
(45) Date of Patent: Jun. 5, 2001

(54) PROCESS FOR PREPARING PRIMARY AMINOORGANOSILANES

(75) Inventors: Steven Gedon, Williamstown; Melinda Hale, Belmont, both of WV (US)

(73) Assignee: Crompton Company, Greenwich, CT (US)

( * ) Notice: Subject to any disclaimer, the term of this patent is extended or adjusted under 35 U.S.C. 154(b) by 0 days.

(21) Appl. No.: 09/730,191

(22) Filed: Dec. 5, 2000

(51) Int. Cl.⁷ .................................................. C07F 7/10
(52) U.S. Cl. ............................................................. 556/413
(58) Field of Search ............................................... 516/413

(56) References Cited

U.S. PATENT DOCUMENTS

| | | |
|---|---|---|
| 3,046,295 | 7/1962 | Llsanke . |
| 5,117,024 | 5/1992 | Dinh et al. . |
| 5,808,123 | * 9/1998 | Balduf et al. ................ 556/413 |

OTHER PUBLICATIONS

Kazimierczuk, R. et al., Synthesis of 3–Aminopropyltriethoxysilane via Catalytic Hydrogenation of 2–Cyanoethyltriethoxysilane, *Appl. Organometal. Chem.* 14, (2000) pp. 160–163.

* cited by examiner

*Primary Examiner*—Paul F. Shaver
(74) *Attorney, Agent, or Firm*—Shirley S. Ma

(57) ABSTRACT

A process is provided for preparing a primary aniinoorganosilane in which a cyanoorganosilane is reacted with hydrogen under hydrogenation conditions and in the substantial absence of water in the presence of a catalytically effective amount of sponge cobalt to produce the primary aminoorganosilane.

23 Claims, No Drawings

PROCESS FOR PREPARING PRIMARY AMINOORGANOSILANES

BACKGROUND OF THE INVENTION

This invention relates to a process for preparing primary aminoorganosilanes. More particularly, the present invention relates to a process for preparing a primary aminoorganosilane by the catalyzed reaction of a cyanoorganosilane with hydrogen.

A process of the foregoing type is described in U.S. Pat. No. 5,117,024. In accordance with this process, a cyanoorganosilane is reacted with hydrogen gas in the presence of a supported cobalt catalyst at a temperature of from about 100EC to 200EC and a pressure within a range of from about 200 psig to 2000 psig. The process is said to provide near quantitative selectivity for the desired primary aminoorganosilane without the production of hydrogen chloride and without the addition of ammonia and solvent systems as in then prior known processes.

A significant disadvantage to the process for making primary aminoorganosilanes described in U.S. Pat. No. 5,117,024 lies in its use of a supported cobalt catalyst. Such a catalyst is typically supplied in the passivated state, i.e., the cobalt particles are covered with a layer of oxide, in order to reduce the hazard of spontaneous combustion of the metal in an oxygen-containing environment such as air. Before the catalyst can be used, it must be activated, generally by reduction with hydrogen at fairly high temperatures, e.g., 500EC and even higher.

SUMMARY OF THE INVENTION

In accordance with the present invention, a process for preparing a primary aminoorganosilane is provided which comprises reacting a cyanoorganosilane with hydrogen under hydrogenation conditions and in the substantial absence of water in the presence of a catalytically effective amount of sponge cobalt to produce the primary aminoorganosilane.

In contrast to a process which employs a passivated cobalt catalyst which is believed to be the case with the process of U.S. Pat. No. 5,117,024 discussed supra, there is no need to activate the sponge cobalt catalyst employed in the process of this invention. Thus, the process of this invention utilizes the catalyst directly and without any need for a prior treatment which would only add to the complexity and expense of the process.

It is further a feature of the invention to conduct the hydrogenation of a cyanoorganosilane to provide the corresponding primary aminoorganosilane employing any suitable catalyst wherein an alkali metal alkoxide is present in the reaction medium to inhibit or suppress the formation of secondary aminoorganosilane.

DESCRIPTION OF THE PREFERRED EMBODIMENTS

The starting cyanoorganosilane reactant herein is preferably one possessing the general formula

in which case the product primary aminoorganosilane will conform to the general formula

wherein each $R^1$ group is independently selected from the group consisting of alkyl and alkoxy radical of from 1 to about 10 carbon atoms, and $R^2$ is a divalent hydrocarbon radical of from 1 to about 20 carbon atoms.

The $R^1$ radical can be, for example, methyl, ethyl, propyl, isopropyl, butyl, tert-butyl, isobutyl, pentyl, dodecyl, methoxy, ethoxy, propoxy, isopropoxy, butoxy, phenyl and phenoxy. $R^1$ is preferably selected from the group consisting of methyl, methoxy, ethyl and ethoxy.

The divalent radical $R^2$ can be, for example, a divalent radical of an alkane, cycloalkane, or an aromatic or aralkane compound. Thus, divalent radical $R^2$ can be, for example, a linear or branched alkylene group such as methylene, ethylene, 1,2-propylene, 1,3-propylene, 2-methyl-1,3-propylene, 3-methyl-1,3-propylene, 3,3-dimethyl-1,3-propylene, ethylidene or isopropylidene, a cycloalkylene group such as cyclohexylene or cycloheptylene, an arylene group such as phenylene, tolylene, xylylene or naphthylene, or the divalent group —$C_6H_4$—$R^3$— in which $R^3$ is 10 methylene, ethylene, ptopylene, etc.

Examples of cyanoorganosilanes which can be hydrogenated by the process of this invention include 2-cyanoethyltrimethysilane, 2-cyanoethyldimethylmethoxysilane, 2-cyanoethylmetbyldimethoxysilane, 2-cyanoethyltrimethoxysilane, 2-cyanoethyldimethylsilane, 2yanoethyldimethoxylsilane, 2-cyanoethyltriethoxysilane, 2-cyanoethyldimethylethoxysilane, 2-cyanoethylphenymethylsilane, 2-cyanoethylphenylmethoxysilane, 3-cyanomethyltriethoxysilane, 3cyanopropyltrtethylsilane, 3-cyanopropylmethyldimethylsilane and 3-cyanopropylmethyldimethoxysilane.

The reaction of the starting cyanoorganosilane with hydrogen in the presence of sponge cobalt catalyst to provide the desired primary aminoorganosilane in accordance with this invention can be carried out in known and conventional high pressure reactors. The reactor can be, for example, a fixed bed, stirred-bed or fluidized-bed type reactor. The process can be run as a batch process or as a continuous process. A stirred-bed reactor is preferred. The reaction tends to be rapid and is generally determined by the amount of catalyst, the pressure of the reactor, reaction temperature and related factors as appreciated by those skilled in the art. In general, residence times of from about 0.2 hours to about 5.0 hours provide acceptable results When the process is run as a batch process, it is generally preferred to use residence times of from about 0.5 to about 3.0 hours accompanied by the addition of hydrogen as it is consumed by the reaction.

It is preferred that the process herein be carried out in the presence of a molar excess of hydrogen, preferably two or more moles of hydrogen per mole of the selected cyanoorganosilane starting reactant. In general, the greater the amount of hydrogen present, the faster the reaction. Therefore, in a preferred mode of operating the process, hydrogen is added in excess at a concentration sufficient to maintain the pressure within the reactor within the range of from about 200 psig to about 2000 psig, and more preferably within the range of from about 500 psig to about 1000 psig, since these pressures permit the use of standard high pressure reactors.

The present process can conventionally be conducted at a temperature within the range of from about 50EC to about 250EC, and preferably at from about 100EC to about 200EC.

The sponge cobalt catalyst employed in the process of this invention can conveniently be selected from among any of several kinds that are commercially available, e.g., Raney7 cobalt, type 2724, from W. R. Grace and Co-0138P from Englehard Corp. If desired and for particular applications, the sponge cobalt can be combined with one or more other catalytically active components, e.g., one or more metals of Group 6B and/or 8B of the Periodic Table of the Elements such as chromium, nickel and/or iron. These metals can be combined with the sponge cobalt catalyst employing any known or conventional process such as doping.

The amount of sponge cobalt catalyst employed in the process of this invention, can vary widely provided, of course, that a catalytically effective amount of the catalyst is present. Useful amounts of sponge-cobalt catalyst can range from about 0.05 to about 20 weight percent, and preferably from about 0.5 to about 1 weight percent, based on the weight of the cyanoorganosilane reactant.

It is convenient to add the sponge cobalt catalyst to the reactor as a slurry, e.g., in a quantity of the intended product primary aminoorganosilane. While the starting cyanoorganosilane could also be utilized for this purpose, it is preferable not to do so since on standing, there may be a tendency of the cyano functionality to result in some poisoning of the catalyst.

The presence of liquid water and/or water vapor is to be substantially avoided as water tends to result in polymerization of some product primary aminoorganosilane to a polysiloxane. It is therefore advantageous to purge the reactor, once sealed, with an inert gas such as nitrogen to substantially remove any water that may be present.

The process of this invention can, if desired, be conducted in the presence of an organic solvent as the use of an organic solvent may increase the rate and/or yield of the process without, however, significantly affecting its selectivity for the desired primary aminoorganosilane. The organic solvent can be a polar or non-polar solvent with a polar solvent, for example, an alkanol such as methanol, ethanol, propanol or isopropanol, being preferred. When using an alkanol solvent, it is preferred that the allanol correspond to any alkoxy group(s) $R^1$ that may be present in the starting cyanoorganosilane reactant in order to minimize or avoid transesterification. Thus, where the starting cyanoorganosilane contains one or more methoxy groups (e.g., as in the case of the reactants 2-cyanoethyldimethylnethoxysilane, 2-cyanoethylmethyldimethoxysilane, 2-cyanoethyltrimethoxysilane, 2-cyanoethyldimethoxysilane, 2-cyanoethylphenylmethoxysilane and 3-cyanopropylmethyldimethoxysilane), the alkanol solvent of choice would be methanol. When the process is conducted as a batch process, it is preferred that the solvent be present at from about 5 to about 50 weight percent, and preferably from about 10 to about 20 weight percent, of the total reaction mixture. When the process is conducted as a continuous process and a solvent is utilized, the starting cyanoorganosilane reactant can be diluted in the solvent with the cyanoorganosilane comprising from about 50 to about 95 weight percent, and preferably from about 80 to about 90 weight percent, of the liquid feed to the reactor.

It is advantageous to conduct the process of this invention in the presence of a substantially anhydrous base, e.g., an alkali metal alkoxide such as lithium methoxide, lithium ethoxide, sodium methoxide, sodium ethoxide, potassium methoxide, potassium ethoxide, anhydrous ammonia, their combinations, and the like, to suppress or inhibit the production of secondary aminoorganosilane. Of these bases, the alkali metal alkoxides are preferred. In general, the amount of base added can range from about 0.01 to about I weight percent, and preferably from about 0.05 to about 0.1 weight percent, based on the weight of the sponge cobalt catalyst.

When using an alkoxide for the aforestated purpose, a solvent, e.g., the parent alkanol of the alkoxide, can conveniently be used as a vehicle for incorporating the alkali metal alkoxide in the reaction medium. Thus, e.g., lithium methoxide can be added as a solution in methanol, sodium ethoxide as a solution in ethanol, etc. When at least one $R^1$ group in the starting cyanoorganosilane reactant is an alkoxy group, in order to minimnize or avoid transesterification, it is preferable to use an alkali metal alkoxide corresponding to the alkoxy group and, as solvent for the alkoxide, the corresponding alkanol. Thus, e.g., when at least one $R^1$ group is a methoxy group, the preferred alkoxide would be a methanol solution of an alkali metal methoxide such as lithium methoxide, sodium methoxide or potassium methoxide.

As previously stated, it is also a particular aspect of this invention to prepare a primary aminoorganosilane by the catalyzed reaction of a cyanoorganosilane with hydrogen under substantially anhydrous conditions in the presence of any suitable catalyst therefor, e.g., sponge cobalt catalyst as previously described or the supported cobalt catalyst of U.S. Pat. No. 5,117,024, and in the presence of the aforesaid alkali metal alkoxide to inhibit or suppress the formation of secondary aminoorganosilane. Optionally, this reaction can additionally employ a different substantially anhydrous base such as anhydrous ammonia to contribute to the suppression of secondary amine formation.

The product primary aminoorganosilane can be recovered by any known or conventional procedure for separating liquid-solid mixtures and mixtures of liquids, for example, filtration andlor distillation.

Primary aminoorganosilanes that can be produced by the present process include, for example, 3-aminopropyltrimethylsilane, 3-aminopropyldimethylmethoxysilane, 3-aminopropylmethyldimethoxysilane, 3-aminopropyltrirnethoxysilane, 3-aminopropyldimethylsilane, 3-aminopropyldimethoxysilane, 3-aminopropyltriethoxysilane, 3-aminopropyldimethylethoxysilane, 3-aminopropylphenylmethylsilane, 3-aminopropylphenylmethoxysilane, 2-aminoethyltrietioxysilane, 4-aminobutyltrinethylsilane, 4-aminobutyldimethysilane and 4-aminobutylmethyldimethoxysilane.

The following examples are illustrative of the process of this invention for obtaining primary aminoorganosilanes.

EXAMPLE 1

In a 2 liter autoclave containing a magnadrive stirrer, cooling coil, and sample tube for sampling, was added 1000 g of distilled cyanoethyltrimethoxysilane. A slurry of 7.1 g of cobalt catalyst (W. R. Grace, Raney® cobalt, type 2724) in 10 mls of 3-aminopropyltrimethoxysilane (Crompton Corp./OSi Specialities, Silquesto A-1110 Silane), was combined with 0.6 mls of 25% sodium methoxide in methanol solution (Aldrich Chemical Co.,) and allowed to stir for one hour prior to addition to the reactor. Upon addition of the catalyst slurry, the reactor was sealed, purged with nitrogen and then twice pressurized with 200 psig hydrogen and vented to atmospheric pressure. The reactor was then pressurized to 500 psi with hydrogen and heated to 145EC with agitation. The reaction was allowed to continue for five hours, or until hydrogen uptake appeared to have stopped, before cooling to room temperature, venting, and discharging the reactor contents. Samples were taken periodically during the reaction with the progress of the reaction being shown in Table I as follows:

TABLE I

| Time (hrs) | Nitrile (wt %) | Primary Amine (wt %) | Secondary Amine (wt %) | Uneluted Heavies (wt %) |
| --- | --- | --- | --- | --- |
| 1 | 73.7 | 22.6 | 0.41 | 0.49 |
| 2 | 46.0 | 49.9 | 0.83 | 0.5 |
| 3 | 23.7 | 72.1 | 1.48 | 0.5 |
| 4 | 8.5 | 85.5 | 1.9 | 0.2 |
| 5 | 1.47 | 88.8 | 1.1 | 5.9 |

Nitrile = cyanoethyltrimethoxysilane.
Primary amine = 3 aminopropyltrimethoxysilane.
Secondary amine = Bis-[3-(trimethoxysilyl)propyl]amine.

EXAMPLE 2

In a 2 liter autoclave containing a magnadrive stirrer, cooling coil, and sample tube for sampling, was added 1000 g of distilled cyanoethyltrimethoxysilane. A slurry of 2.5 g of sponge cobalt catalyst (W.R. Grace, Raney® cobalt, type 2724) in 10 mls of 3-aminopropyltrimetboxysilane (Crompton Corp./OSi Specialties, Silquest® A-1110 Silane), and 0.5 mls of a 1 M lithium methoxide in methanol solution (Aldrich Chemical Co.) were combined and allowed to stir for one hour prior to addition to the reactor. The reactor was sealed, purged with nitrogen and then twice pressurized with 200 psig hydrogen and vented to atmospheric pressure. The reactor was then pressurized to 500 psi with hydrogen and heated to 145EC with agitation. The reaction was allowed to continue for three hours, or until hydrogen uptake appeared to have stopped, before cooling to room temperature, venting, and discharging the reactor contents. Samples were taken periodically during the reaction with the progress of the reaction being shown in Table II as follows:

TABLE II

| Time (hrs) | Nitrile (wt %) | Primary Amine (wt %) | Secondary Amine (wt %) | Uneluted Heavies (wt %) |
| --- | --- | --- | --- | --- |
| 0.5 | 92.0 | 5.77 | 0 | 0 |
| 1 | 77.7 | 16.9 | 3.44 | 0 |
| 1.5 | 58.6 | 31.6 | 6.98 | 0 |
| 2 | 33.3 | 54.8 | 8.5 | 0.7 |
| 2.5 | 7.9 | 79.0 | 9.98 | 0.3 |
| 3 | 1.9 | 86.8 | 10.17 | 0 |

Nitrile = cyanoethyltrimethoxysilane.
Primary amine = 3-aminopropyltrimethoxysilane.
Secondary amine = Bis-[3-trimethoxysilyl)propyl]amine.

EXAMPLE 3

In a 1 liter Parr autoclave containing a magnadrive stirrer, cooling coil, and sample tube for sampling, was added 500 g of distilled cyanoethyltrimethoxysilane and a slurry of 1.5 g of sponge cobalt catalyst (W. R. Grace, Raney® cobalt, type 2724) in 10 mls of 3-aminopropyltrirnethoxysilane (Crompton Corp./OSi Specialties, Silquest® A-1110 Silane). The reactor was sealed, purged with nitrogen and then twice pressurized with 200 psig hydrogen and vented to atmospheric pressure. The reactor was then pressurized to 500 psi with hydrogen and heated to 160EC with agitation. The reaction was allowed to continue for three hours, or until hydrogen uptake appeared to have stopped, before cooling to room temperature, venting, and discharging the reactor contents. Samples were taken periodically during the reaction with the progress of the reaction being shown in Table III as follows:

TABLE III

| Time (hrs) | Nitrile (wt %) | Primary Amine (wt %) | Secondary Amine (wt %) | Uneluted Heavies (wt %) |
| --- | --- | --- | --- | --- |
| 0.5 | 89.8 | 5.78 | 1.2 | 0 |
| 1 | 72.056 | 16.25 | 5.8 | 2.9 |
| 1.5 | 56.1 | 26.25 | 9.5 | 4.5 |
| 2 | 34.4 | 43.5 | 13.7 | 5.6 |

Nitrile = cyanoethyltrimethoxysilane.
Primary amine = 3-aminopropyltrimethoxysilane.
Secondary amine = Bis-[3-(trimethoxysilyl)propyl]amine.

EXAMPLE 4

In a 2 liter autoclave containing a magnadrive stirrer, cooling coil, and sample tube for sampling, was added 1106 g of cyanoethyltrimethoxysilane, and a slurry of 6.0 g of sponge cobalt catalyst (W. R. Grace, Raney® cobalt, type 2724) in 10 mls of 3-aminopropyltrimethoxysilane (Crompton Corp./OSi Specialties, Silquest A-1110 Silane). The reactor was sealed, purged with nitrogen and then twice pressurized with 200 psig hydrogen and vented to atmospheric pressure. The reactor was then pressurized to 500 psi with hydrogen and heated to 150EC with agitation. The reaction was allowed to continue for three hours, or until hydrogen uptake appeared to have stopped, before cooling to room temperature, venting, and discharging the reactor contents. Samples were taken periodically during the reaction with the progress of the reaction being shown in Table IV as follows:

TABLE IV

| Time (hrs) | Nitrile (wt %) | Primary Amine (wt %) | Secondary Amine (wt %) | Uneluted heavies (wt %) |
| --- | --- | --- | --- | --- |
| 0.5 | 59.461 | 31.77 | 2.38 | 3.4 |
| 1 | 1.804 | 82.14 | 7.38 | 6.3 |
| 1.5 | 1.506 | 82.15 | 10.5 | 4.17 |

Nitrile = cyanoethyltrimethoxysilane.
Primary Amine = 3-aminopropyltrimethoxysilane.
Secondary amine = Bis-[3-(trimethoxysilyl)propyl]amine.

EXAMPLE 5

In a 2 liter autoclave containing a magnadrive stirrer, cooling coil, and sample tube for sampling, was added 1000 g of distilled cyanoethyltrimethoxysilane and a slurry of 3.1 g of unpromoted sponge cobalt catalyst (W. R. Grace, Raney® cobalt, type 2724) in 10 mls of 3-aminopropyltrimethoxysilane (Crompton Corp./OSi Specialities, Silquest® A-1110 Silane) with agitation. The reactor was sealed, purged with nitrogen and then twice pressurized with 200 psig hydrogen and vented to atmospheric pressure. To the reactor was then added 30.4 g of anhydrous ammonia, and then pressurized to 500 psi with hydrogen. The reactor was then heated to 154EC and the stirrer speed increased to 1000 rpm. The reaction was allowed to continue for three hours, or until hydrogen uptake appeared to have stopped, before cooling to room temperature, venting, and discharging the reactor contents. Samples were taken periodically during the reaction with the progress of the reaction being shown in Table V as follows:

TABLE V

| Time (hrs) | Nitrile (wt%) | Primary Amine (wt %) | Secondary Amine (wt %) | Uneluted Heavies (wt %) |
|---|---|---|---|---|
| 0.5 | 88.0 | 10.5 | 0.33 | 0 |
| 1 | 71.0 | 25.8 | 1.6 | 0 |
| 2 | 32.75 | 62.0 | 2.2 | 1.0 |
| 3 | 6.1 | 89.8 | 1.9 | 0.5 |

Nitrile = cyanoethyltrimethoxysilane.
Primary amine = 3-aminopropyltrimethoxysilane.
Secondary amine = Bis-[3-(trimethoxysilyl)propyl]amine.

EXAMPLE 6

In a 2 liter autoclave containing a magnadrive stirrer, cooling coil, and sample tube for sampling was added 989 g of distilled cyanoethyltrimethoxysilane. A slurry of 6.5 g of sponge cobalt catalyst (W. R. Grace, Raney® cobalt, type 2724) in 10 mils of 3-aminopropyltrimethoxysilane (Crompton Corp./OSi Specialities, Silquest® A-1110 Silane) was combined with 0.5 ml of a 25% sodium methoxide in methanol solution (Aldrich Chemical Co.) and allowed to stir for one hour prior to addition to the reactor. The reactor was sealed, purged with nitrogen and then twice pressurized with 200 psig hydrogen and vented to atmospheric pressure. To the reactor was then added 42.3 g of anhydrous ammonia, and then pressurized to 500 psi with hydrogen. The reactor was subsequently heated to 160EC and the stirrer speed increased to 1000 rpm. The reaction was allowed to continue for three hours, or until hydrogen uptake appeared to have stopped, before cooling to room temperature, venting, and discharging the reactor contents. Samples were taken periodically during the reaction with the progress of the reaction being shown in Table VI as follows:

TABLE VI

| Time (hrs) | Nitrile (wt%) | Primary Amine (wt %) | Secondary Amine (wt %) | Uneluted Heavies (wt %) |
|---|---|---|---|---|
| 0.5 | 86.98 | 18.047 | 0 | 0 |
| 1 | 22.3 | 77 | 0 | 0 |
| 1.5 | 2.45 | 94 | 1 | 0 |

Nitrile = cyanoethyltrimethoxysilane.
Primary amine = 3-aminopropyltrimethoxysilane.
Secondary amine = Bis-[3-(trimethoxysilyl)propyl]amine.

EXAMPLE 7

In a 2 liter autoclave containing a magnadrive stirrer, cooling coil, and sample tube for sampling, was added 1022 g of distilled cyanoethyltrimethoxysilane. A slurry of 2 g of sponge cobalt catalyst (Engelhard Corp.,) in 10 mls of 3-aminopropyltrimethoxysilane (Crompton Corp./OSi Specialities, Silquest® A-1110 Silane) was added to the reactor. The reactor was sealed, purged with nitrogen, and then twice pressurized with 200 psig hydrogen and vented to atmospheric pressure. To the sealed reactor was then added 29.3 g of anhydrous ammonia, and then pressurized to 500 psi with hydrogen. The reactor was then heated to 160EC and the stirrer speed increased to 100 rpm. The reaction was allowed to continue for three hours, or until hydrogen uptake appeared to have stopped, before cooling to room temperature, venting, and discharging the reactor contents. Samples were taken periodically during the reaction with the progress of the reaction being shown in Table VII as follows:

TABLE VII

| Time (hrs) | Nitrile (wt%) | Primary Amine (wt %) | Secondary Amine (wt %) | Uneluted Heavies (wt %) |
|---|---|---|---|---|
| 0.5 | 96.6 | 2 | 0 | 0 |
| 1 | 84.7 | 10.6 | 2.2 | 0 |
| 1.5 | 68.7 | 21.95 | 2.2 | 0 |
| 2 | 52.431 | 33.6 | 1.1 | 0 |
| 3 | 7.77 | 74.2 | 10.2 | 0 |

Nitrile = cyanoethyltrimethoxysilane.
Primary amine = 3-aminopropyltrimethoxysilane.
Secondary amine = Bis-[3-(trimethoxysilyl)propyl]amine.

What is claimed is:

1. A process for preparing a primary aminoorganosilane which comprises reacting a cyanoorganosilane with hydrogen under hydrogenation conditions and in the substantial absence of water in the presence of a catalytically effective amount of sponge cobalt to produce the primary aminoorganosilane.

2. The process of claim 1 wherein the cyanoorganosilane possesses the general formula $R^1_3 Si R^2 CN$ and the product primary aminoorganosilane possesses the formula $R^1_3 Si R^2 CH_2NH_2$ wherein each $R^1$ group is independently selected from the group consisting of alkyl and alkoxy radical of from 1 to about 10 carbon atoms and $R^2$ is a divalent hydrocarbon radical of from 1 to about 20 carbon atoms.

3. The process of claim 2 wherein each $R^1$ radical is independently selected from the group consisting of methyl, ethyl, propyl, isopropyl, butyl, tert-butyl, isobutyl, pentyl, dodecyl, methoxy, ethoxy, propoxy, isopropoxy, butoxy, phenyl and phenoxy and the $R^2$ radical is selected from the group consisting of methylene, ethylene, 1,2-propylene, 1,3-propylene, 2-methyl-1,3-propylene, 3-methyl-1,3-propylene, 3,3dimethyl-1,3-propylene, ethylidene, isopropylidene, cyclohexylene, cycloheptylene, phenylene, tolylene, xylylene, naphthylene and the divalent radical —$C_6H_4$—$R^3$— in which $R^3$ is methylene, ethylene or propylene.

4. The process of claim 4 wherein the cyanoorganosilane is selected from the group consisting of 2-cyanoethyltrimethylsilane, 2-cyanoethyldimethylinethoxysilane, 2cyanoethylmnethyldimethoxysilane, 2-cyanoethyltrimethoxysilane, 2-cyanoethyldimethylsilane, 2-cyanoethyldimethoxysilane, 2-cyanoethyltriethoxysilane, 2-cyanoethyldinethylethoxysilane, 2-cyanoethylphenymethylsilane, 2-cyanoethylphenylmethoxysilane, 3-cyanomethyltriethoxysilane, 3-cyanopropyltrimethylsilane, 3-cyanopropylmethyldimethylsilane and 3-cyanopropylmethyldiinethoxysilane.

5. The process of claim 1 wherein the reaction is carried out in the presence of a molar excess of hydrogen at a pressure of from about 200 psig to about 2100 psig and at a temperature of from about 50EC to about 250EC.

6. The process of claim 1 wherein from about 0.05 to about 20 weight percent sponge cobalt catalyst based on the weight of the cyanoorganosilane is employed.

7. The process of claim 1 wherein from about 0.5 to about 1 weight percent sponge cobalt catalyst based on the weight of the cyanoorganosilane is employed.

8. The process of claim 1 wherein the sponge cobalt catalyst is added as a slurry in a slurry-forming quantity of the desired aminoorganosilane product.

9. The process of claim 1 carried out in the presence of a solvent for the cyanoorganosilane.

10. The process of claim 9 wherein the solvent is a polar solvent.

11. The process of claim 2 carried out in the presence of a solvent for the cyanoorganosilane.

12. The process of claim 11 wherein at least one to group of the cyanoorganosilane is an alkoxy group.

13. The process of claim 12 wherein the solvent for the cyanoorganosilane is an alkanol corresponding to alkoxy group $R^1$ of the cyanoorganosilane.

14. The process of claim 1 carried out in the presence of an anhydrous base.

15. The process of claim 14 wherein the anhydrous base is an alkali metal alkoxide.

16. The process of claim 15 wherein the alkali metal alkoxide is selected from the group consisting of lithium methoxide, lithium ethoxide, sodium methoxide, sodium ethoxide, potassium methoxide and potassium ethoxide.

17. The process of claim 15 wherein the alkali metal alkoxide is provided as a solvent solution thereof.

18. The process of claim 15 wherein the alkali metal alkoxide is provided as a solution thereof in an alkanol corresponding to that of the alkoxide.

19. The process of claim 2 carried out in the presence of an alkali metal alkoxide, wherein at least one $R^1$ group of the cyanoorganosilane is an alkoxy group and the alkoxide moiety of the alkali metal alkoxide corresponds to alkoxy group $R^1$.

20. The process of claim 19 wherein the alkali metal alkoxide is provided as a solution thereof in an alkanol corresponding to that of the alkoxide.

21. A process for preparing a primary aminoorganosilane which comprises reacting a cyanoorganosilane with hydrogen under hydrogenation conditions in the substantial absence of water in the presence of a catalytically effective amount of hydrogenation catalyst and in the presence of a secondary aminoorganosilane formation-suppressing amount of alkali metal alkoxide.

22. The process of claim 12 wherein the hydrogenation catalyst is a supported cobalt catalyst.

23. The process of claim 12, wherein the alkali metal alkoxide is selected from the group consisting of lithium methoxide, lithium ethoxide, sodium methoxide, sodium ethoxide, potassium methoxide and potassium ethoxide.

* * * * *